United States Patent [19]
Kasra et al.

[11] Patent Number: 6,126,691
[45] Date of Patent: Oct. 3, 2000

[54] BONE PROSTHESIS FIXATION DEVICE AND METHODS OF USING SAME

[75] Inventors: Mehran Kasra; Marc D. Grynpas, both of Toronto, Canada

[73] Assignee: Mount Sinai Hospital Corporation, Toronto, Canada

[21] Appl. No.: 09/011,467

[22] PCT Filed: Jun. 16, 1997

[86] PCT No.: PCT/CA97/00416

§ 371 Date: Apr. 17, 1998

§ 102(e) Date: Apr. 17, 1998

[87] PCT Pub. No.: WO97/48352

PCT Pub. Date: Dec. 24, 1997

Related U.S. Application Data

[60] Provisional application No. 60/019,997, Jun. 18, 1996.

[51] Int. Cl.[7] .............................. A61F 2/30; A61F 2/32; A61F 2/38; A61B 17/56; A61B 17/58
[52] U.S. Cl. ............................... 623/18.11; 623/20.34; 623/20.36; 623/23.26; 623/23.27; 606/63; 606/68
[58] Field of Search .................. 623/16–23; 606/60, 606/68, 70, 71, 72, 73, 74

[56] References Cited

U.S. PATENT DOCUMENTS

| | | | |
|---|---|---|---|
| 2,490,364 | 12/1949 | Livingston . | |
| 4,237,875 | 12/1980 | Termanini . | |
| 4,599,086 | 7/1986 | Doty . | |
| 4,904,267 | 2/1990 | Bruce et al. . | |
| 5,032,134 | 7/1991 | Lindwer . | |
| 5,037,422 | 8/1991 | Hayhurst et al. | 606/72 |
| 5,303,718 | 4/1994 | Krajicek | 606/60 |
| 5,441,538 | 8/1995 | Bonutti . | |
| 5,472,452 | 12/1995 | Trott | 606/72 |
| 5,522,845 | 6/1996 | Wenstrom, Jr. | 606/72 |
| 5,569,251 | 10/1996 | Baker et al. . | |
| 5,601,564 | 2/1997 | Gustilo et al. . | |
| 5,620,443 | 4/1997 | Gertzbein et al. . | |
| 5,632,748 | 5/1997 | Beck, Jr. et al. | 606/89 |
| 5,649,963 | 7/1997 | McDevitt | 606/72 |
| 5,658,335 | 8/1997 | Allen | 606/61 |
| 5,702,391 | 12/1997 | Lin | 606/60 |
| 5,800,547 | 9/1998 | Schafer et al. | 623/17 |
| 5,800,550 | 9/1998 | Sertich | 623/17 |

FOREIGN PATENT DOCUMENTS

| | | |
|---|---|---|
| 0 403 028 | 6/1990 | European Pat. Off. . |
| 78 22070 | 7/1978 | France . |
| 91 03149 | 11/1991 | France . |
| 36 08 163 A 1 | 3/1986 | Germany . |
| 38 38 388 A 1 | 11/1988 | Germany . |
| 43 27 054 C1 | 8/1993 | Germany . |
| 94 02 598 U | 2/1994 | Germany . |

OTHER PUBLICATIONS

D.R. Carter et al, Journal of Orthopaedic Research, 6:726–748, 1988.
R. Huiskes, Acta. Orthop. Scand. (Suppl.) 185, 1–208, 1980.
A. Rohlman et al., Journal of Biomechanics, 21:605–611, 1988.
R. Winquist et al., Journal of Bone and Joint Surgery, 66–A, No. 4, 1984.
K.D. Johnson et al., Journal or Orthopaedic Trauma, vol. 1 No. 1, pp. 1–11, 1987.

*Primary Examiner*—Michael J. Milano
*Assistant Examiner*—Tram A. Nguyen
*Attorney, Agent, or Firm*—Bereskin & Parr

[57] ABSTRACT

A fixation mechanism for use in a prosthesis implantable into bone comprises a main body defining an internal passageway and including a plurality of openings extending between the internal passageway and the exterior of the main body. The device has a plurality of bone engaging members, with each bone engaging member being mounted in a respective opening for movement between a retracted position in which the bone engaging member does not extend outside the body, and an extended position in which the bone engaging member extends through the respective opening into surrounding bone to secure the device. A plunger within the main body is adapted to directly or indirectly engage the bone engaging members to displace the bone engaging members out through their respective openings.

24 Claims, 12 Drawing Sheets

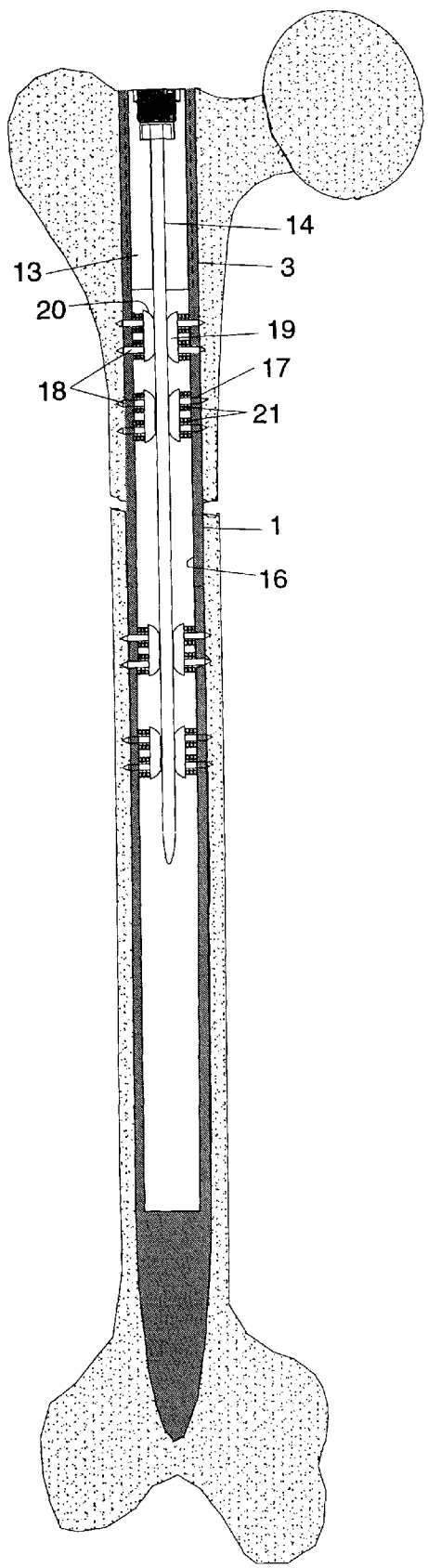
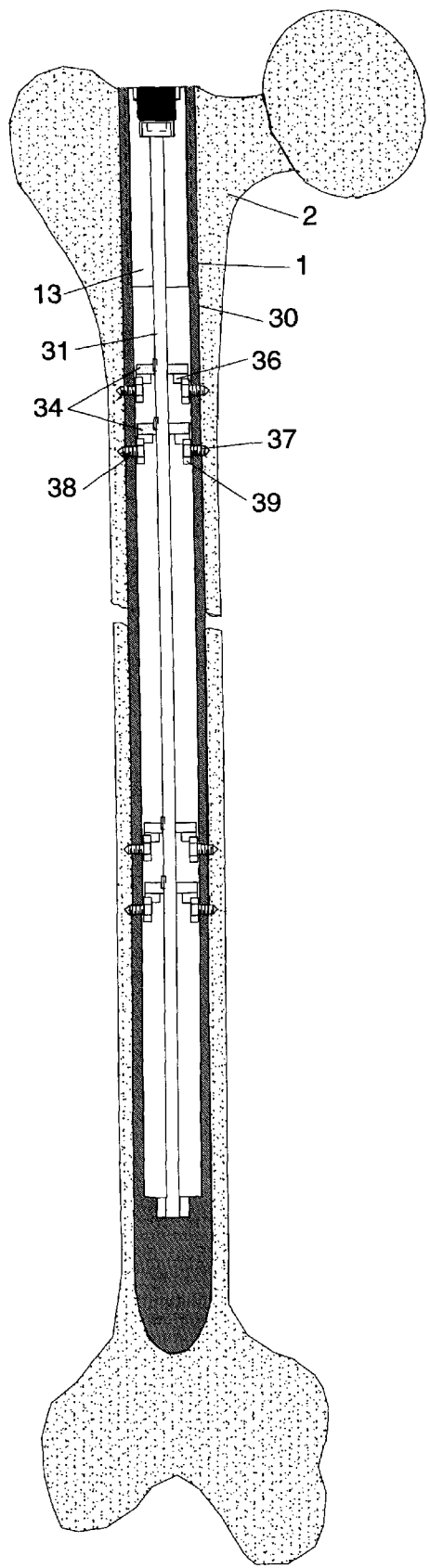
FIGURE 10
FIGURE 11

BONE PROSTHESIS FIXATION DEVICE AND METHODS OF USING SAME

This application claims benefit of Provisional Application Ser. No. 60/019,997 filed Jun. 18, 1996.

FIELD OF THE INVENTION

The present invention relates to a bone prosthesis fixation device, a bone prosthesis comprising the device, and a method of implanting such a bone prosthesis. This invention can be applied to a variety of orthopaedic and dental implants. A particular application of the invention is to the fixation of intramedullary fixation devices within a bone cavity, such as total hip stem prostheses, or intramedullary rods.

BACKGROUND OF THE INVENTION

Existing prostheses fixation mechanisms use cement, screw, or press-fit techniques to obtain initial stability between the bone and implant. Adequate initial stability using these fixation mechanisms may not be achieved due to loosening of the implant, or fracturing of the bone. For example, the stability of a non-cemented total hip stem prosthesis is achieved by carefully impacting the implant to the broached, contoured proximal femur. This primary fixation may be followed by secondary fixation such as osseointegration and porous in-growth. However, considerable force is usually required to securely seat a press-fit prosthesis. Thus at surgery there is a concern about fracturing the femur. Furthermore, excessive hydrostatic stress or excessive shear strain in mesenchymal tissue between a newly implanted material and bone results in mesenchymal cells differentiating into fibrous tissue (D. R. Carter et al, Journal of Orthopaedic Research, 6:726–748, 1988). Therefore, no bone ingrowth happens, and eventually the implant becomes loose. Excessive hydrostatic stress can be caused by a very tight fit (press-fit) inhibiting capillary blood flow to the tissue and decreasing tissue oxygen tension. Excessive shear strain is caused by an inadequate press-fit which permits large micromotions. Also when an intramedullary stem is used, the medullar cavity is cleaned, broached, and reamed to some extent. In this procedure a part of the vascularity system that nourishes the bone is, at least temporarily disturbed, especially in the diaphyseal region. Therefore, it is better to keep the reaming and broaching to a minimum level. Theoretically, for bone ingrowth to occur, a porous coated implant must be rigidly fixed with close apposition to the bone, without causing excessive stresses and strains at the bone-implant interface. However, this would require the medullar cavity to be prepared to very tight tolerances. In practice, this press fit technique requires an interference fit between the prosthesis and the bone, thus creacting large stresses. Accordingly, it is important that the broaching and contouring of the femur be carried out carefully and exactly. This results in operations being more lengthy and more complex. Additionally the severe impacts required to achieve a press fit for the prosthesis result in this technique being suitable only for younger patients. For older patients with thinner or more brittle bones, this technique is therefore not applicable.

Instead, for older patients, where there is a higher demand for hip prostheses and the like, the prosthesis is often fixed with cement. However, this has its own problems. The adhesive commonly used, PMMA, is strongly exothermic and shrinks after it is set. There are also significant problems in obtaining a good bond between the bone cement and the bone. After a period of use, the cement can sometimes tend to break down or parts of it can break away. While researchers have looked for other, more suitable cements, no truly suitable cements have been found.

Another problem is obtaining a proper stiffness of prosthesis stem which is compatible with that of the bone. For example, choosing a stem with a low stiffness will result in poor fixation, while a stem with high stiffness causes bone necrosis due to stress shielding. With high stiffness, loads can be transmitted from the lower end of the prosthesis, in a hip prosthesis, and bone around the head of the prosthesis is largely unloaded, an effect known as "stress shielding". Studies assuming concentric cylindrical geometries for the bone and prosthesis have predicted that use of lower stiffness stems can reduce stress shielding (R. Huiskes, Acta. Orthop. Scand. (Suppl.) 185, 1–208, 1980) but can increase relative motion (A. Rohlmann et al., Journal of Biomechanics, 21:605–611, 1988). This results in a trade-off between stress shielding and relative motion for cementless hip implants. What is required is a prosthesis which combines a stiffness close to that of the bone (low stiffness) and a good fixation mechanism.

Prosthesis fixation can be more problematic in cases dealing with low bone stock and long operating time, such as; prosthesis fixation in a revision surgery or fixation of an intramedullary rod for management of a traumatic long bone fracture.

Revision surgery is much more complex and technically much more difficult than first time surgery, and requires prolonged operating time. Therefore any fixation mechanism design leading to reducing the operating time is valuable. One of the major problems inherent with revision surgery is bone loss. Therefore, any procedure causing more reduction in bone stock, such as reaming, should be avoided if possible. In this case, bone stock in the metaphysis is often insufficient for internal fixation devices and revision with a custom long-stemmed component to act as an intramedullary rod across the defect is a viable technique.

Closed intramedullary fixation with or without interlocking screws has been a widely accepted and well-documented method of management of long bone fractures, especially femoral shaft fractures. Complication of closed intramedullary fixation of femoral shaft fractures includes bursting of the proximal fracture component during insertion of the rod and inadequate fixation of the fracture. This may result in proximal migration of the rod, malrotation of the fracture components, or axial shortening of the femur. These complications may result in delayed union, malunion, or shortening of the extremity or may necessitate premature removal of the rod.

The stability of nonlocked rods relies only on frictional contact with bone, requiring reaming of the intramedullary canal. The reaming procedure causes considerable vascular damage and also reduces the mechanical resistance of bone to burst fracture caused by hoop stresses during insertion. Implantation of a medullary rod without previous reaming causes relatively minor damage to the blood circulation and maintains its mechanical integrity. Because of this, reaming should be performed only to such an extent as to ensure sufficient fracture stabilization. Using an undersized rod requires no or minor reaming and reduces the insertion force, and therefore, reduces the chance of bursting fracture significantly. However, using an undersized rod reduces the axial push out forces significantly, resulting in unstable fixation.

The friction between the rod and the endosteal cortex may inhibit the rod from completely recovering its original untwisted shape after release of a torsional load (spring back angle). This is an important point clinically because a small spring back angle implies that a large residual malrotation deformity can result from torsional loading after load release. Considering the type and location of fracture both proximal and distal locking screws may be in place to recover some of the torsional deformation. The locking screws provide resistance to axial and torsional loading. They also help to prevent toggling of the rod in the femoral canal. However, locked rods, require drilling the bone for inserting the locking screws. Locking screws are prone to fatigue failure, and their fixation requires a long operating time.

Using pins as an anchoring means has been suggested for the fixation of cementless prostheses, as in U.S. Pat. No. 5,032,134 and French published patent application 78/22070. Pins have also been suggested for fixation of a cemented prosthesis stem. U.S. Pat. No. 4,904,267 reports driving barbed pins into the bone tissue by a suitable tool. The intention is that the cement will bond with the pins, and the prosthesis itself will be bonded to the cement in an entirely conventional manner. A driving mechanism for the pins is not explained. The patent also discloses numerous other complex techniques, including the provision of an expandable annular member, actuated by a bolt extending through the prosthesis.

In fixation of a noncemented prosthesis stem, Lindwer (U.S. Pat. No. 5,032,134) describes the use of two cooperating elements, one surrounding the other to form the complete prosthesis. One prosthesis element adjacent the bone is provided with pins distributed along the outer face and located inside the outer face when the prosthesis is being inserted. After insertion, the pins are driven out of the outer face, in order to cause them to penetrate into the bone. The disadvantage of this design is that it is only the first prosthesis element that is fixed into the bone by the pins. The second prosthesis element is, as in conventional techniques, press-fitted albeit to the first element. Again, considerable impacts will be required to wedge the second element in place. Therefore, initially, the whole prosthesis assembly is held in the bone only by pins. In this case, a large number of the pins described in Lindwer are required to secure the prosthesis and hold the first prosthesis element securely enough to resist the impacts produced by press-fitting the second prosthesis element into the first one, without fracturing the bone. According to tests by the present inventors, pins penetrating into trabecular bone do not have enough holding power to secure the prosthesis, and a large number of pins penetrating into cortical bone may fracture the bone. Also, using two prosthesis elements requires a longer surgery time. The present inventors have also discovered that there is a possibility of jamming when a strip of pins are driven into the bone.

Published French Patent Application (78/22070) proposes that pins be driven outwardly into the bone through holes in the wall of endoprosthesis by fluid pressure or by a flexible rod. A driving mechanism using fluid pressure is not practical, since a very high fluid pressure would be required, resulting in problems of leakage and high manufacturing costs. A flexible rod as proposed in the French Patent Application would not have enough rigidity to force the pins into the cortical bone. This design has not been completed into a practical embodiment.

It is desirable to extract a prosthesis particularly in cases where a prosthesis is damaged, loose, or infected. In all the above-mentioned patents/applications it is very difficult, and in some cases impossible to remove the pins without breaking the bone. In particular, the anchoring pins in U.S. Pat. No. 5,032,134 and French published application 78/22070 include no means for their removal. Cleaning out of the cement and array of pins described in U.S. Pat. No. 4,904, 267, would be extremely difficult, if at all possible.

Furthermore, anchorage of pins into trabecular bone contributes very little in fixation of the implant while anchorage of pins into cortical bone creates a strong fixation. However, in a diseased bone which may be very fragile, there is a high chance that penetration of pins into cortical bone causes fracture. Therefore, it is preferable to provide other fixation means and mechanisms, besides driving pins, for a fragile bone.

SUMMARY OF THE INVENTION

The present invention provides a system and a method to improve the fixation of a cementless implantable bone prosthesis by driving pins or screws, from the inside of a hollow prosthesis stem fitted into the bone. Two different mechanisms are introduced, one for driving staples or pins into the bone which is an improvement of the fixation systems using simple pins, and the other for driving screws into the bone introducing a fixation system suitable for both normal and fragile bone.

The system and method of the invention provide many advantages including the following:

(1) the chances of fracturing of the bone while fitting the implant into the bone cavity are significantly reduced, since the fitting does not have to be very tight and precise to obtain initial stability;

(2) as a consequence of (1) relatively, less reaming and broaching (or no reaming and broaching) are required for preparation of the bone cavity resulting in less damage to the bone vascular system;

(3) initial stability can be reinforced by anchoring pins (e.g. staples), or screws into the bone, allowing for secondary fixation by osseointegration and porous in-growth;

(4) using pins in pairs eliminates the possibility of jamming when pins are driven into the bone;

(5) since the fitting is not required to be very tight, and due to the presence of better initial stability (less micromotion), the stresses and strains on cells are low which in turn allows better osseointegration;

(6) by using a hollow stem, with or without an insert, having a proper length and material, the stiffness of the prosthesis stem can be adjusted comparable to that of the bone, therefore, preventing stress shielding;

(7) use of self tapping pointed screws with sharp threads for penetration into fragile bones reduces the possiblity of fractures;

(8) surgery time is reduced, and (9) the pins or screws can be removed easily when extraction of the prosthesis is required.

The systems, devices and methods of the invention are particularly suited for use in the managment of bone fractures. Intramedullary rods fixed to bone using the fixation mechanisms described herein have many advantages in addition to those set out above. A slightly undersized intramedullary rod using a fixation mechanism described herein can be inserted easily minimizing potential fracturing of the bone, while maintaining rigid fixation. Stability can also be obtained with short rods. An intramedullary rod with a fixation mechanism described herein minimizes malrotation, and it recovers its original shape after the release of a torsional load. The prosthesis of the invention allows the use of undersized rods thereby eliminating or reducing the need for reaming which typically causes vascular damage. A prosethesis of the invention does not require conventional locking screws, since the penetrated pins or screws can perform the load transfer and maintain stability uniformly along the bone. Optimum numbers of the pins or screws can be selected and distributed along the bone wherever they are needed, having regard to the type and location of a fracture, to effectively distribute the load among the pins or screws The pins or screws used in the prosthesis of the present invention are exposed to shear stresses rather than to the large bending stresses which occur with conventional locking screws. The invention does not create any bone defect compared with conventional locking screws. In this case, the operating time is significantly reduced.

The systems, devices and methods of the present invention are also well suited for revision surgery. This invention reduces the need for most custom implant designs that have been needed for revision in the past. The stem component using a staple or screw fixation mechanism described herein requires no reaming or minimal reaming which saves the bone stock. It does not damage the vascular system as with the press fitted stems. It can also be fitted easily while providing a rigid fixation, therefore, reducing the operating time.

Broadly stated the present invention provides a fixation device for fixing a prosthesis to a bone, the device comprising:
(a) a main body defining an internal passageway and including a plurality of openings extending between the internal passageway and the exterior, the main body being implantable into a cavity in bone;
(b) a plurality of bone engaging members, with each bone engaging member being mounted in a respective opening for movement between a retracted position in which the bone engaging member does not extend outside the body, and an extended position in which the bone engaging member extends through the respective opening into surrounding bone to secure the device; and
(c) displacing means within the main body adapted to directly or indirectly engage the bone engaging members to displace the bone engaging members out through their respective openings.

The fixation device may be an integral part of a prosthesis or a separate part attached to a prosthesis by a coupling mechanism. Therefore, the invention also contemplates a prosthesis device comprising a fixation device of the invention, a prosthesis device coupled to a fixation device of the invention, and a method for fixing a prosthesis to a bone using the fixation device.

In an embodiment of the invention, the bone engaging members are pins, and the displacing means comprise plunger means slidably mounted within the body and having a first end extending out of the body for actuation thereof, and a second end adapted to engage the pins to displace the pins out through the openings.

In accordance with an embodiment of the present invention, there is provided a prosthetic device implantable into skeletal bone, the device comprising:
(a) a main body defining an internal passageway and including a plurality of openings extending between the internal passageway and the exterior, the body being implantable into a cavity in skeletal bone;
(b) a plurality of pins, with each pin being mounted in a respective opening for sliding movement between a retracted position in which the pin does not extend outside the body and an extended position in which the pin extends through the respective opening into surrounding bone to secure the device;
(c) a common pin head secured to and joining two or more pins; and
(d) plunger means slidably mounted within the body and having a first end extending out of the body for actuation thereof and a second end adapted to engage the pin heads to displace the pin heads out through the openings.

The pins may be effectively provided in pairs, joined by common pin heads, so as to form staples. Preferably, the pin heads and the second end of the plunger means include cooperating cam surfaces. The pins are preferably arranged so that the pin heads are mounted in pairs abutting each other in a rest position, and the pins include spring means biasing the pin heads towards one another.

In accordance with another aspect of the present invention, there is provided a method of mounting a prosthetic device as defined above, the method comprising driving the plunger into the body using a plurality of impacts, and providing at least one minute of recovery time after each impact.

In a preferred embodiment, the present invention, provides a prosthetic device implantable into skeletal bone, the device comprising:
(a) a main body implantable into skeletal bone, and having a straight axis, an internal passageway around the axis, a plurality of openings extending between the internal passageway and the exterior thereof, a head offset from the axis of the main body and a top surface offset from the head and generally perpendicular to the axis of the main body onto which top surface the internal passageway opens;
(b) pins provided within the internal passageway and displaceable between a retracted position within the internal passageway and an extended position extending out through the openings and penetrating bone;
(c) drive means for displacing the pins between the retracted and extended positions; and
(d) an actuating rod means extending from the drive means to a position adjacent the top surface, for actuation of the drive means.

In a second embodiment of the fixation device of the invention, the bone engaging members are screws, and the displacing means are rotatably mounted in the body. Preferably the screws are adapted to penetrate bone and they are threadably mounted in an opening in the main body. The screws may contain a gear at one end which interacts with the displacing means resulting in rotation of the screws and penetration of the screws into the bone.

Therefore, the present invention also provides, a prosthetic device implantable into skeletal bone, the device comprising:
(a) a main body defining an internal passageway and being implantable into skeletal bone, and having a plurality of openings extending between the internal passageway and the exterior, each opening being threaded;
(b) a plurality of screws, each screw being threadably mounted in a respective opening, being adapted to penetrate bone and including a gear at an end thereof;
(c) an actuating means rotatably mounted in the body; and
(d) drive gear means mounted on the actuating means and meshing with the gears on the screws, whereby rotation of the actuating means rotates the screws.

In a device of the invention using a gear mechanism, preferably the flank length of the teeth of the crown gears is sufficiently long relative to the length of the teeth of the spur gears that the teeth of the spur gears mesh continuously with the teeth of the crown gears as the screws are rotated from a retracted position to an extended position. Thus, as the screws are screwed into the passageway, the spur gears slide along the teeth of the crown gears. The length of the flanks of the crown gear teeth should accordingly be longer than the flank length of the spur gear teeth by an amount at least equal to the expected travel of the screws.

In accordance with another aspect of the present invention, there is provided a method of implanting a prosthetic device as defined above into one or more bone segments the method comprising mounting the prosthesis into a cavity in bone, and actuating the actuation means to cause the screws to rotate and to penetrate bone smoothly and progressively.

A prosthetic device of the invention may comprise a prosthesis for a hip, which includes a prosthesis head and a top surface offset to one side of the head, wherein the internal passageway of the body is straight and opens onto the top surface, and is generally perpendicular hereto. A prosthetic device of the invention may also be used as an intermedullary rod or nail for repositioning and fixing segments of bone. A prosthetic device of the invention may also be used as a revision for a joint, in particular as a knee revision. One or more of the devices of the present invention may be integrated into femoral modular and tibial tray components or they can be coupled using a coupling device such as a pin and guide coupling mechanism or a coupling screw.

BRIEF DESCRIPTION OF THE DRAWINGS

For a better understanding of the present invention, and to show more clearly how it may be carried into effect, reference will now be made, by way of example, to the accompanying drawings, which show preferred embodiments of the present invention and in which:

FIG. 10 is a sectional view through an embodiment of the present invention as shown in FIGS. 1 and 2, in an intramedullar rod;

FIG. 11 is a sectional view through an embodiment of the present invention as shown in FIGS. 3 and 4, in an intramedullar rod;

DESCRIPTION OF THE PREFERRED EMBODIMENTS

The invention will now be described in detail with reference to the accompanying drawings.

Figure 1:
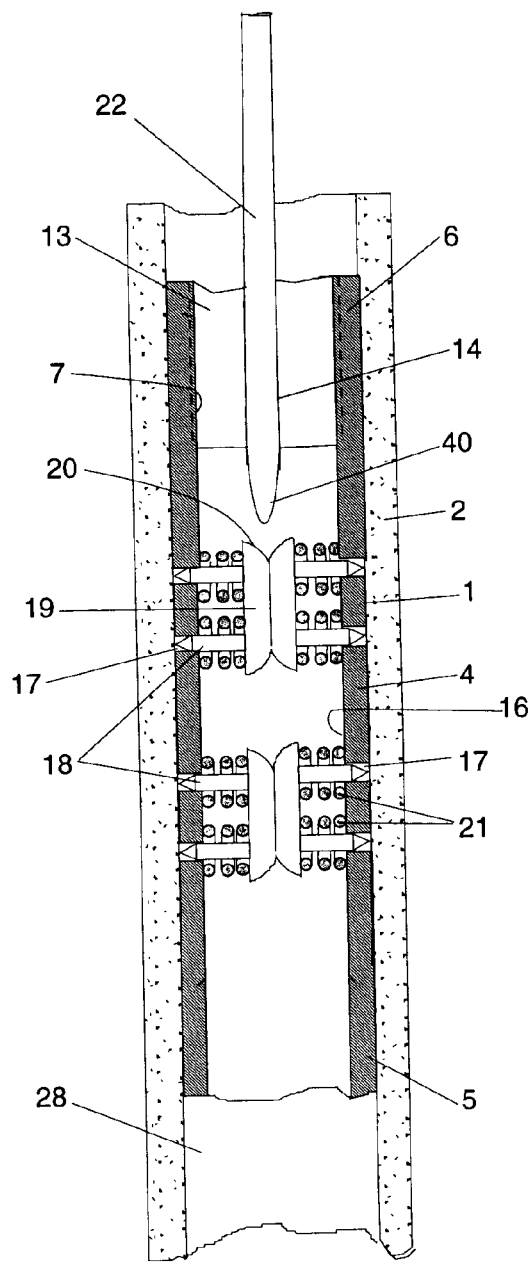
FIG. 1 is a sectional view through an embodiment of a fixation device of the invention showing pins as the bone engaging members, before the pins have been driven into the bone.
Figure 2:
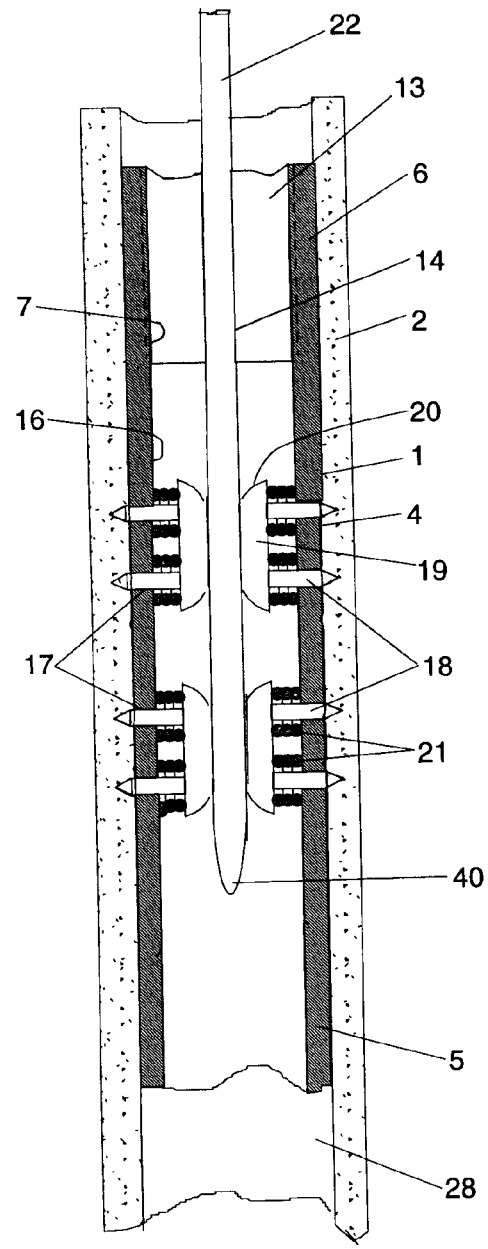
FIG. 2 is a view similar to FIG. 1, after pins have been driven into the bone.

As shown in FIGS. 1 and 2, a fixation device of the present invention comprises a main body 4 which has a lower part 5, and an upper part 6. The device may be an integral part of a prosthesis stem or it can be a separate part attached to a prosthesis by a coupling mechanism. The size and shape of the main body are selected so that it fits within a cavity formed within a bone 2 to be secured. The main body 4 may be slotted or closed and it may have a straight axis or a curved axis. The materials used to make the fixation device are selected so that it has a stiffness comparable to that of bone to prevent stress shielding.

Through both the lower and upper parts 5, 6 of the fixation device 1, there is an internal passageway 7 with the lower part 5 of the body 4 forming an internal chamber 16. The cross-section of the internal passageway 7 may have any shape for example, it may be circular, eliptical or rectangular. Bone engaging members (e.g. pins or screws) are mounted in openings 17 formed in the body around the internal chamber 16. In the described and illustrated embodiments two vertical rows of diametrically opposite openings 17 are shown. However, a number of different arrangements of the openings 17 can be provided. More particularly, the openings can be provided at more frequent spacings around the circumference of the main body 4, for example at 90°, 60° spacings. Further, there may be advantages in staggering the openings axially, with respect to different angular locations. The number and distribution of the openings are selected based on the type and location of the fracture and to effectively distribute the load.

The prosthesis uses novel fixation devices to fix the prosthesis to the bone. In accordance with an embodiment illustrated in FIGS. 1 and 2, the fixation device 1 comprises pins 18 formed into groups, preferably pairs, with each group of pins 18 secured to a common pinhead 19. The ends of the pin heads 19 may be rounded to provide cam surfaces 20. The pins 18 are mounted in openings 17 around an internal chamber 16 in the main body 4. A suitable spring arrangement, for example helical coil springs 21, may be provided around the pins 18 to bias the pin heads 19 toward one another. By way of example, the pin heads 19 may be biased against one another in pairs.

The pins 18 are moved from a retracted position in which they do not extend outside the body 4 (FIG. 1) to an extended position in which they extend through their respective openings 17 into the bone 2 (FIG. 2), using a plunger 22 which is slidably mounted in the body 4. The body 4 preferably has a guide insert 13 to guide the plunger 22 through a guide channel 14. The plunger 22 includes a tapered end surface 40 defining cam surfaces which cooperate with the cam surfaces 20 of the pin heads 19. The plunger 22, pin heads 19, and pins 18 are made from materials which are sufficiently harder and stiffer than bone so that the pins can be driven into the bone. Preferably, the materials are the same as the stem material so as not to cause any Galvanic corrosion. Examples of materials include metals used in prostheses such as cobalt chromium, or titanium alloys.

In use, a cavity 28 is formed in a bone 2 and a prosthesis using a fixation device 1 is inserted into the cavity 28 (FIG. 1). When the prosthesis is in place in the bone, the plunger 22 is inserted through the guide channel 14, and the pins 18 are extended into the bone 2 (FIG. 2).

Figure 3:
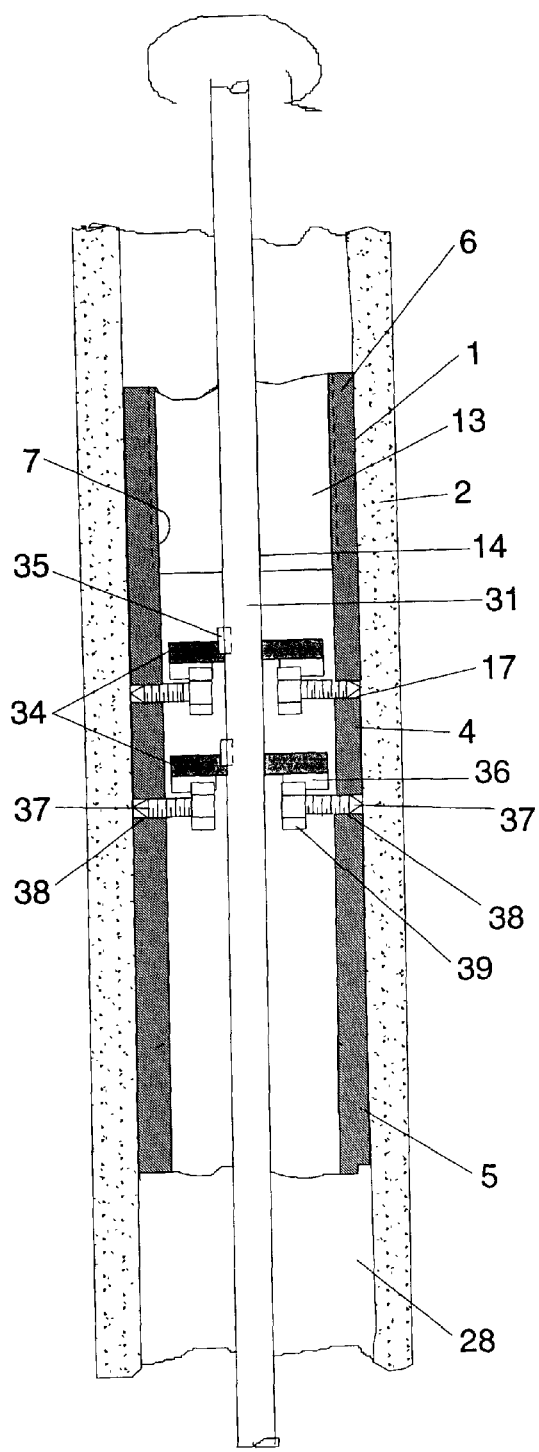
FIG. 3 is a sectional view through an embodiment of a fixation device of the invention fitted within a bone, showing screws as the bone engaging members, before the screws have been driven into the bone.
Figure 4:
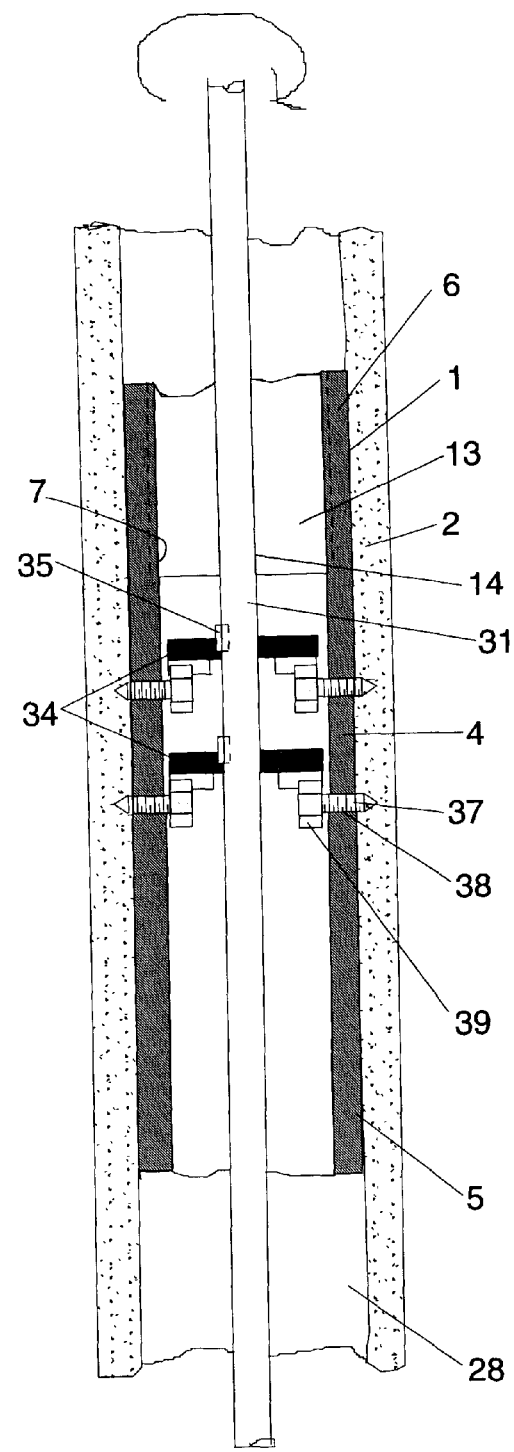
FIG. 4 is a sectional view through an embodiment of a fixation device of the invention showing screws as the bone engaging members, with the screws in the bone.

In accordance with another embodiment illustrated in FIGS. 3 and 4, the fixation device 1 comprises screws 37 which are mounted in threaded openings 38 in the body 4. The screws 37 have a sharp pointed tip and sharp threads which can cut or dig into the bone 2. A spur gear 39 at the inner end of each screw forms a head of the screw. The screws 37 are moved from a retracted position in which they do not extend outside the body 4 (FIG. 3) to an extended position in which they extend through their respective openings 17 into the bone 2 (FIG. 4), by means of an actuating rod 31 which is mounted for rotation in the body 4. The body 4 preferably has a guide insert 13 to guide the actuating rod 31 through a guide channel 14. The actuating rod has crown gears 34 mounted thereon for meshing with a respective spur gear 39 of the screw. The actuating rods and screws are made from materials which are sufficiently hard so that the screws can be driven into the bone. Preferably the materials are the same as those used in the prosthesis main body 4.

In use, a prosthesis using the fixation device 1 is inserted into the cavity 28 in a similar manner to the first embodiment. The actuating rod 31 is rotated and the crown gears 34 on the rod then rotate the spur gears 39 causing the screws 37 to rotate and extend into the bone.

Figure 5:
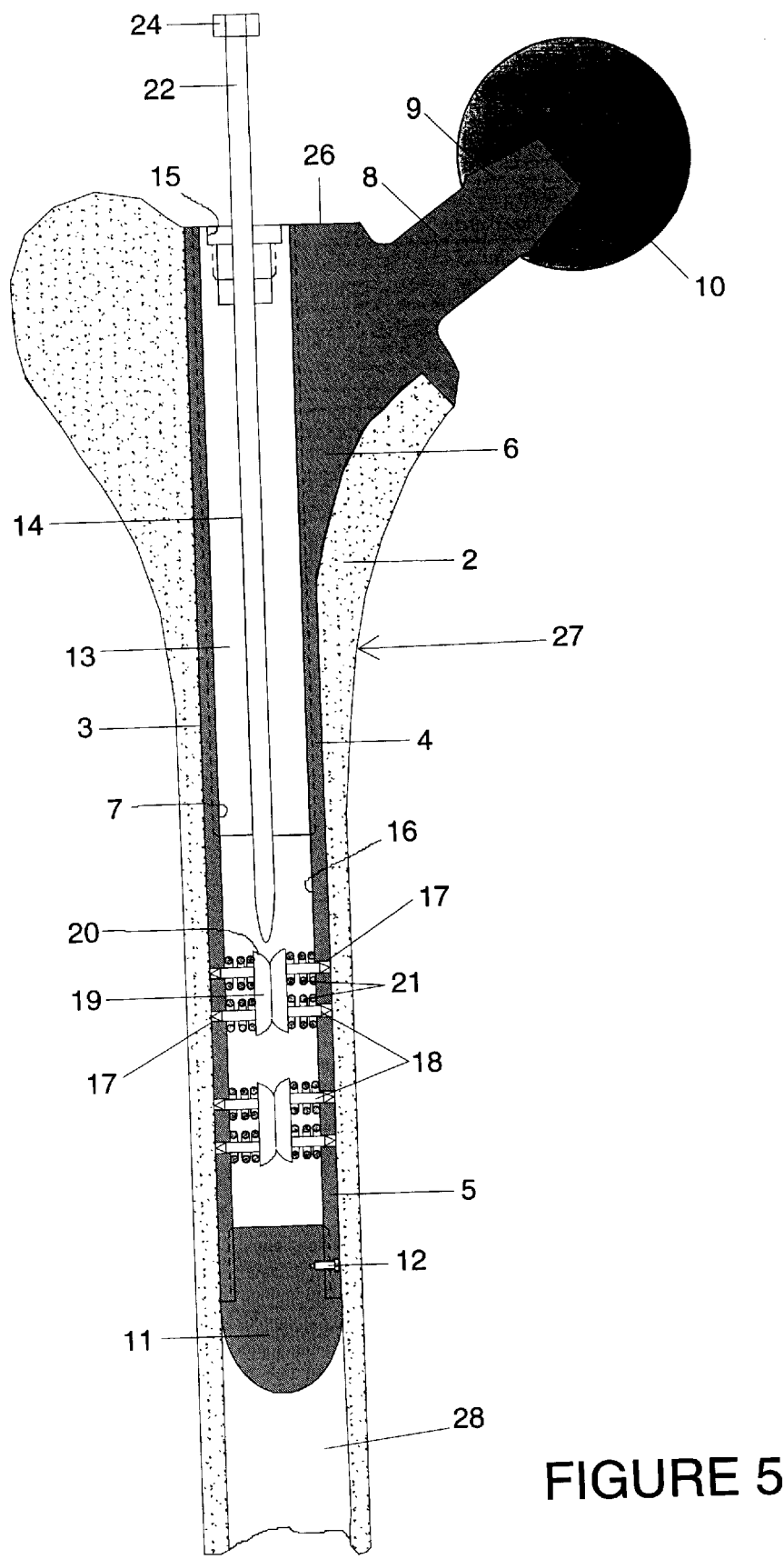
FIG. 5 is a sectional view through an embodiment of a prosthesis in accordance with the present invention, shown fitted within the head of a femur, but before driving of the pins.

Referring to a specific embodiment in FIG. 5, the femoral shaft is indicated at 27. In order to accept a prosthesis with a fixation mechanism according to the present invention, it is prepared with a cavity 28, by known techniques of cleaning, broaching and reaming.

Figure 6:
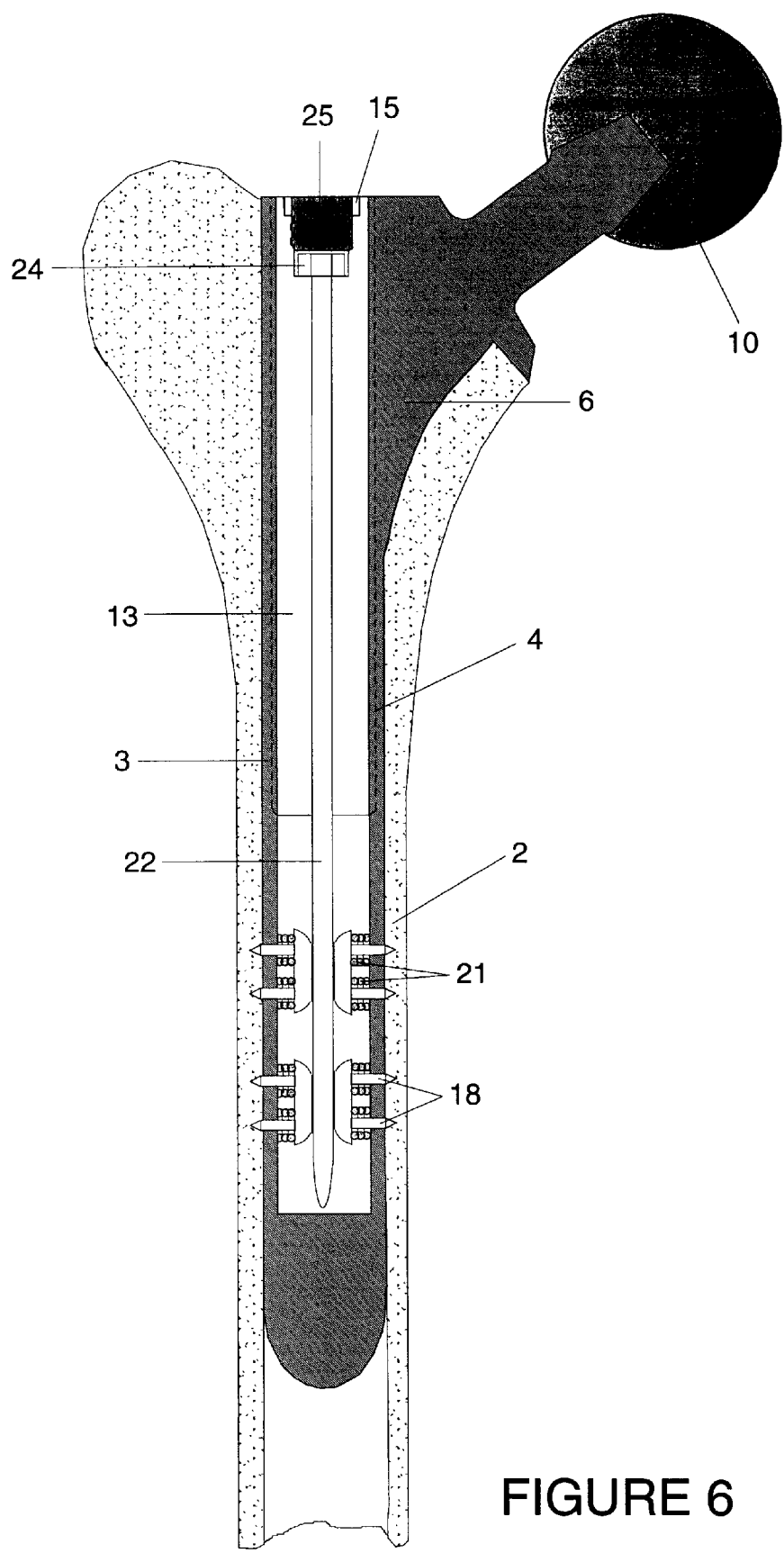
FIG. 6 is a view similar to FIG. 5, after pins have been driven into the bone.
Figure 7:
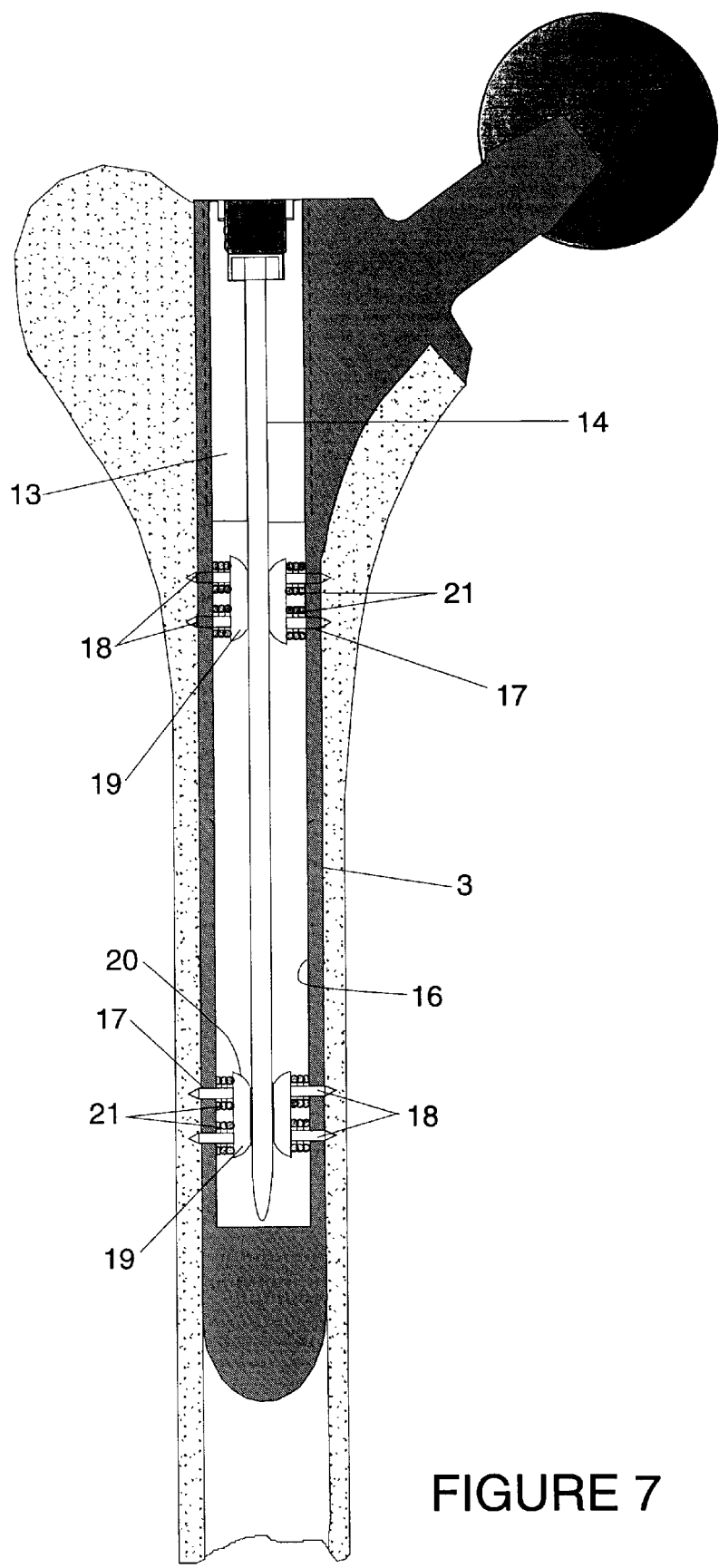
FIG. 7 is a view similar to FIG. 6, with abutting pairs of pins located at different positions.

In FIGS. 5 to 7, the prosthesis 3 comprises a main body 4 which has a lower cylindrical part 5, and an upper enlarged part 6, which form an intramedullary stem. Through both the lower and upper parts 5, 6, there is an internal passageway 7 of constant cross-section. The upper enlarged part 6 continues into a neck 8. Here, the neck 8 is shown as providing a frusto-conical surface 9 on which a generally spherical head 10 is mounted; the head 10 may alternatively be integral with the main body 4.

As shown in FIGS. 5 to 7, the passageway 7 is straight and extends through the length of the main body 4, and is closed at the bottom by a closure member 11 which is generally rounded. The closure member 11 can be adapted to be screwed into the passageway 7, and a locking screw 12 is provided.

At the upper end of the passageway 7, this is again threaded and a guide insert 13 is screwed into this threaded portion of the passageway. The insert 13 defines a narrow guide channel 14, for a plunger. The upper end of this channel 14 is enlarged in two steps, as shown at 15, part of which is threaded, for reasons detailed below. The upper step of the enlargement 15 is formed as an Allen socket or the like, for screw insertion of the insert 13. The length and material of the insert 13 should be chosen to have an optimum stiffness for the prosthesis stem that matches well with that of the bone 2.

The passageway 7, and hence the enlarged part 15, opens onto a top surface 26 which is perpendicular to the axis of the passageway 7. The top surface 26 is offset from the head 10 and at an angle to the neck 8.

Figure 8:
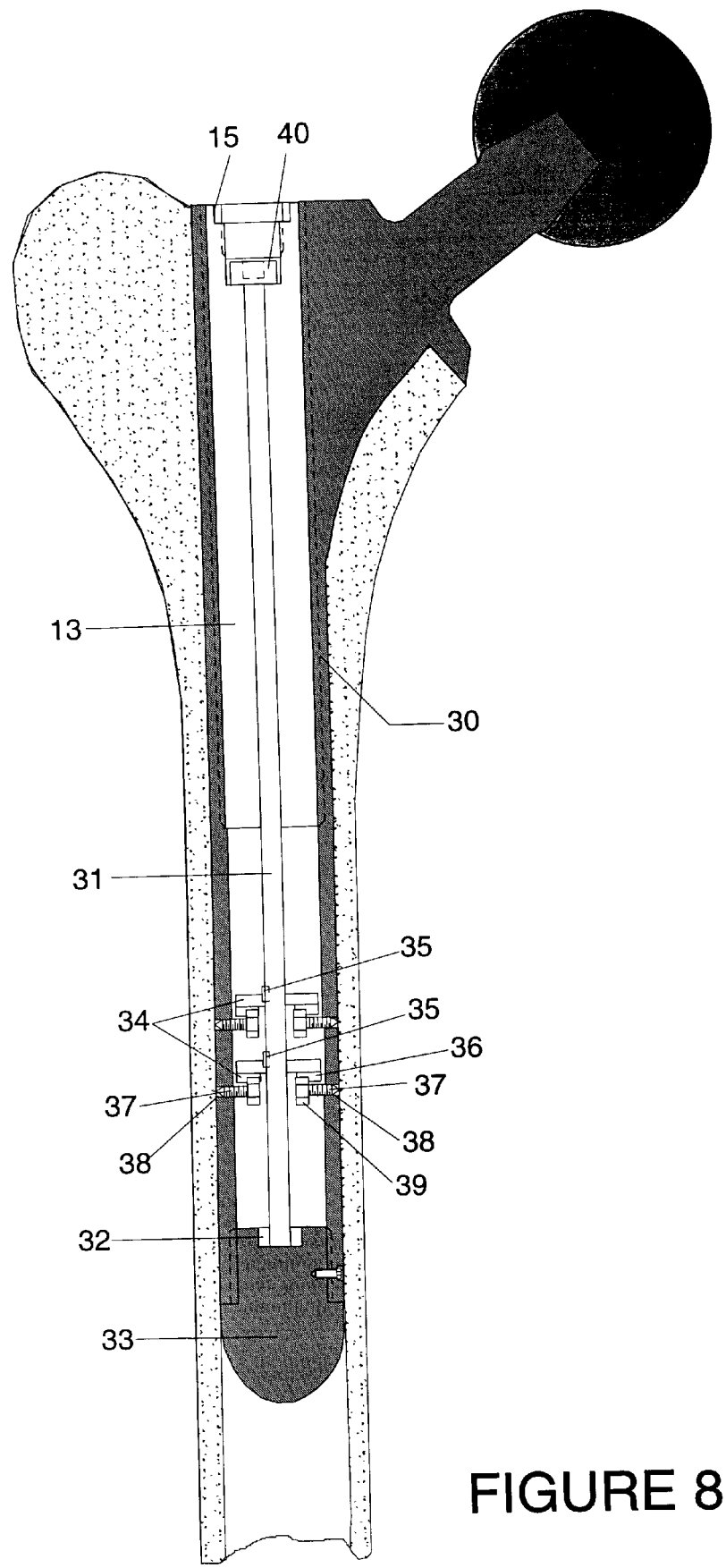
FIG. 8 is a side, sectional view through an embodiment of a prosthesis according to the present invention, before insertion of screw fixing elements.
Figure 9:
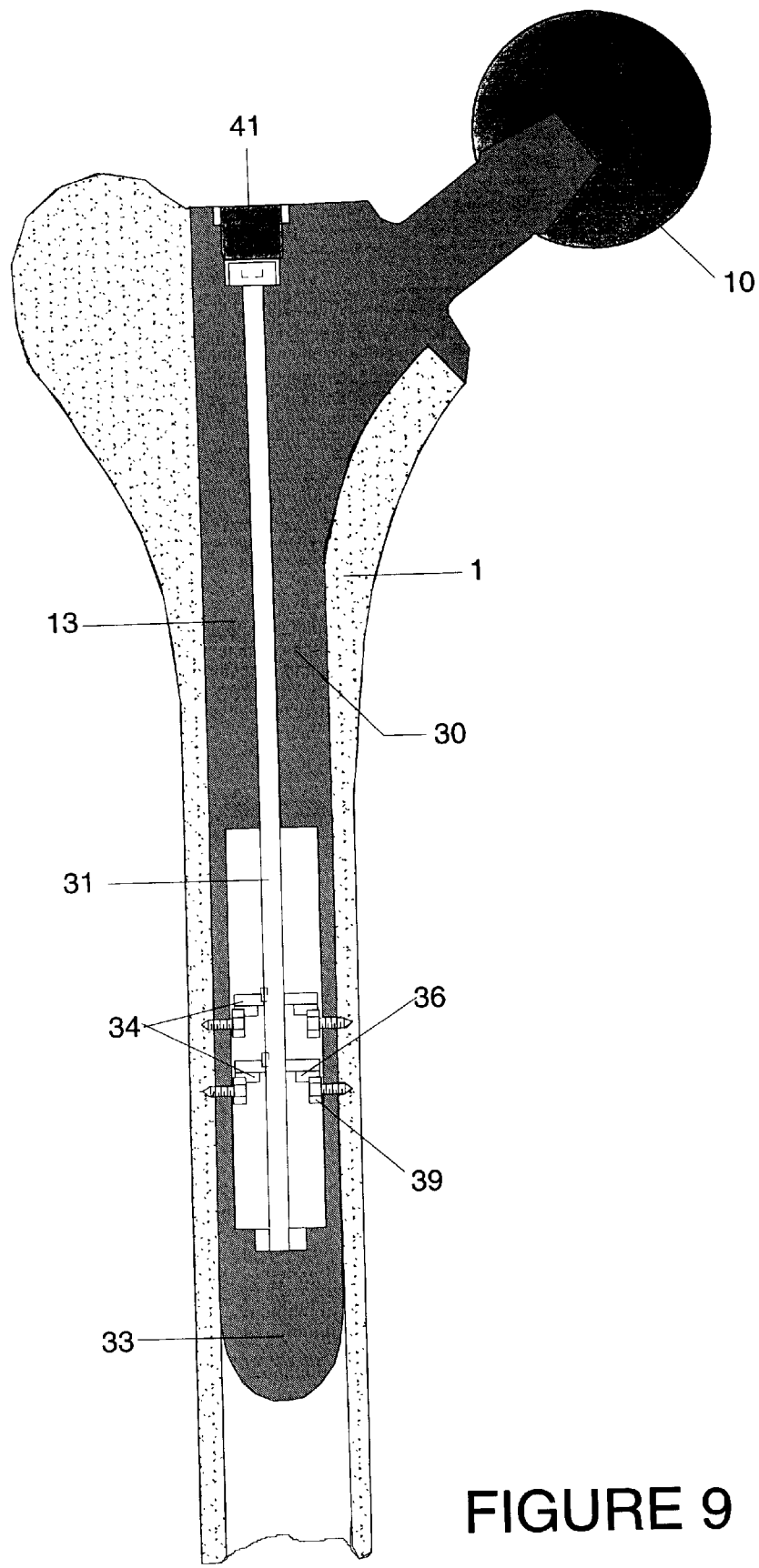
FIG. 9 is a view similar to FIG. 8, after insertion of the screw elements.

Accordingly, between the closure member 11 and guide insert 13, there is an internal chamber 16. Openings 17 are formed in the body 4 around this chamber 16. Two vertical rows of diametrically opposite openings 17 are shown in FIGS. 8 and 9. However, as discussed herein, a number of different arrangements of the opening 17 can be provided.

In the embodiment shown in FIGS. 5 and 6, eight pins 18 are provided on a common plane. More staples or pins could be readily introduced to increase the pull out force required and fixation stiffness, while reducing the individual forces at the penetration sites of each pin, i.e. by distributing the load amongst more pins or staples. The number of pins is selected according to the size of the prosthesis and the location where the pins are to be inserted. To avoid local fracture, it is recommended that the pins be at least 5 mm apart and penetration of the pins into the bones be limited to a maximum of 2 mm.

The pins 18 are provided in pairs with each pair secured to a common pin head 19. As shown, ends of the heads 19 are rounded to provide cam surfaces 20. The openings 17 and pins 19 are preferably arranged so that the pin heads 19 are mounted in pins abutting each other. Abutting pairs can be located at different positions in the chamber 16. FIGS. 5 and 6 show devices with abutting pairs located near to each other, while FIG. 7 shows abutting pairs distant from each other.

Helical coil springs 21 or the like, are provided around the pins 18, to bias the heads 19 towards one another. Any suitable spring arrangement could be provided. Thus, as shown, prior to insertion, the pin heads 19 are biased against one another in pairs.

A plunger 22 is slidably mounted in the guide channel 14. Thus, the guide insert 13 serves both to guide the plunger 22 and to reinforce the upper part of the main body 4. The plunger 22 includes a head 24 and a tapered end surface 40, defining cam surfaces, cooperating with the cam surfaces of the pin heads 19. A nut 25 (FIG. 6) is provided, for engagement with a threaded part of the enlarged portion 15. The plunger 22, heads 19 and pins 18 should all be hard and stiff enough, relative to the bone 2, to enable the pins 18 to be driven into the bone.

In using the embodiment shown in FIGS. 5 to 7, the top of the femur is prepared in the usual way. The head and neck of the original femur are removed, and a cavity formed in the top of the femur. As shown, the lower part of the cavity, within the femur should be generally straight and cylindrical. The upper part is enlarged, to accommodate the upper, enlarged part 6 of the prosthesis 3. This cavity can be formed in a known manner. However, unlike known techniques that rely on force-fitting the prosthesis, it is not necessary for the cavity to be so precisely formed in order to have a successful fit without fracturing the bone. Indeed, it is preferred for the cavity to enable the prosthesis 3 to be initially inserted relatively easily (no interference). To insert the prosthesis 3, if necessary, the top surface 26 can be struck with a mallet or the like to drive the prosthesis 3 into position, and only light impacts should be required.

With the prosthesis fully inserted, as shown in FIG. 5, the plunger 22 is driven down, by means of a mallet or otherwise. The plunger 22 should be inserted gradually by impaction on top of its shaft. It is recommended to use light impacts and at least three impacts with a recovery time of about one minute after each impact, to avoid bone fracture caused by penetration of the pins 18. With the plunger 22 fully inserted, as shown in FIGS. 6 and 7, the staples, comprising the pins 18 and, common pin heads 19 are driven radially outwards, to penetrate the bone. As shown in FIG. 6, a nut 25 is then screwed into the enlargement 15, to secure the head 24 and hence to retain the plunger 22 in position. Completion of the hip joint and the rest of the operation can be carried out as usual.

Reference will now be made to FIGS. 8 and 9 which show another embodiment of the present invention, generally denoted by the reference 30. For simplicity and brevity, like components are given the same reference numeral as in the first embodiment, and the description is not repeated. In the second embodiment, the plunger 22 is replaced by an actuating rod 31. The rod 31 is mounted for rotation in the guide insert 13. Also, the lower end of the rod 31 is received in a bearing 32 in a closure member 33. Bearing 32 is a thrust bearing or the like to prevent upward displacement of the rod 31, and provide the axial thrust for a gear mechanism described below.

Crown gears 34 are mounted on the rod 31 for rotation therewith. They can be secured in any known manner, for example by way of keys 35. The gears 34 have radially extending teeth 36.

The pins 18 of the first embodiment are replaced by screws 37, which engage corresponding threaded openings 38 in the body of the prosthesis 30. The screws 37 each have a sharp pointed tip and sharp threads which can cut or dig into bone.

At the inner end of each screw 37, there is a spur gear 39, forming a head of the screw and meshing with a respective crown gear 34. It is to be noted that the length of the teeth of the crown gears 34 are substantially greater than the length of the teeth of the spur gears 39. The teeth of the gears 34 have a flank width, i.e. a dimension in a radial direction of those gears, so that for all positions of the screws 37, there is complete meshing of the gears 34 and spur gears 39. Preferably, the flank width of the crown gears 34 is around 2 mm longer than the flank width of the spur gears 39. The flank width or length of the crown gear teeth should be greater than that of the spur gear teeth by an amount at least equal to the axial or expected travel of the screws 37. In effect, the spur gears 39 travel radially along the crown gears 34, in use.

The actuating rod 31 includes a head 40 provided with a socket which can be engaged by an Allen key or the like (FIG. 8). As before, a nut 41 is provided for closing the top of the prosthesis (FIG. 9).

This embodiment of the prosthesis 30 can be manufactured in a number of different ways. Thus, the insert 13 can either be a separate component or it can be integral with the body of the prosthesis 30. Further, while the prosthesis 30 is shown with a body that is continuous over the whole axial length, it is possible for the portion containing the gears 34, 39 to be separate from the rest of it. This then permits ready internal access to assemble the gear mechanism. This portion can then be attached to other portions of the prosthesis 30, e.g. by a screw action to complete the prosthesis. The closure member 33 can either be separate and secured by a locking screw, as shown in FIG. 8, or it can be integral with the prosthesis 30. FIG. 9 shows a variant of the second embodiment where the closure member 33 and the insert 13 are both integral with the main body 4 of the prosthesis 3; in this variant, the actual construction should be such as to provide for access to the chamber containing the gears 34, 39 to permit assembly of the gear mechanism.

In use, the prosthesis 30 is inserted in a similar manner to the first embodiment. Again, the cavity in the femur is prepared in a similar way, and the prosthesis 30 inserted, and there is no necessity for a very tight press-fit.

Then an Allen key or the like is engaged with the head of the actuating rod 31 and the rod rotated. The gears 34 then rotate the spur gears 39, causing the screws 37 to rotate and penetrate the bone around the prosthesis. With the screws fully extended, the tips of the screws penetrate the bone to secure the prosthesis in position. The nut 41 is then inserted to complete the prosthesis.

FIG. 10 shows a prosthesis which is an intramedullary rod using the fixation mechanism of FIGS. 1 and 2. FIG. 11 shows an intramedullary rod using the fixation mechanism of FIGS. 3 and 4. Like components are given the same reference numerals as in FIGS. 1 to 4, and the description is not repeated. The intramedullary rod may be slotted or closed.

Figure 12:
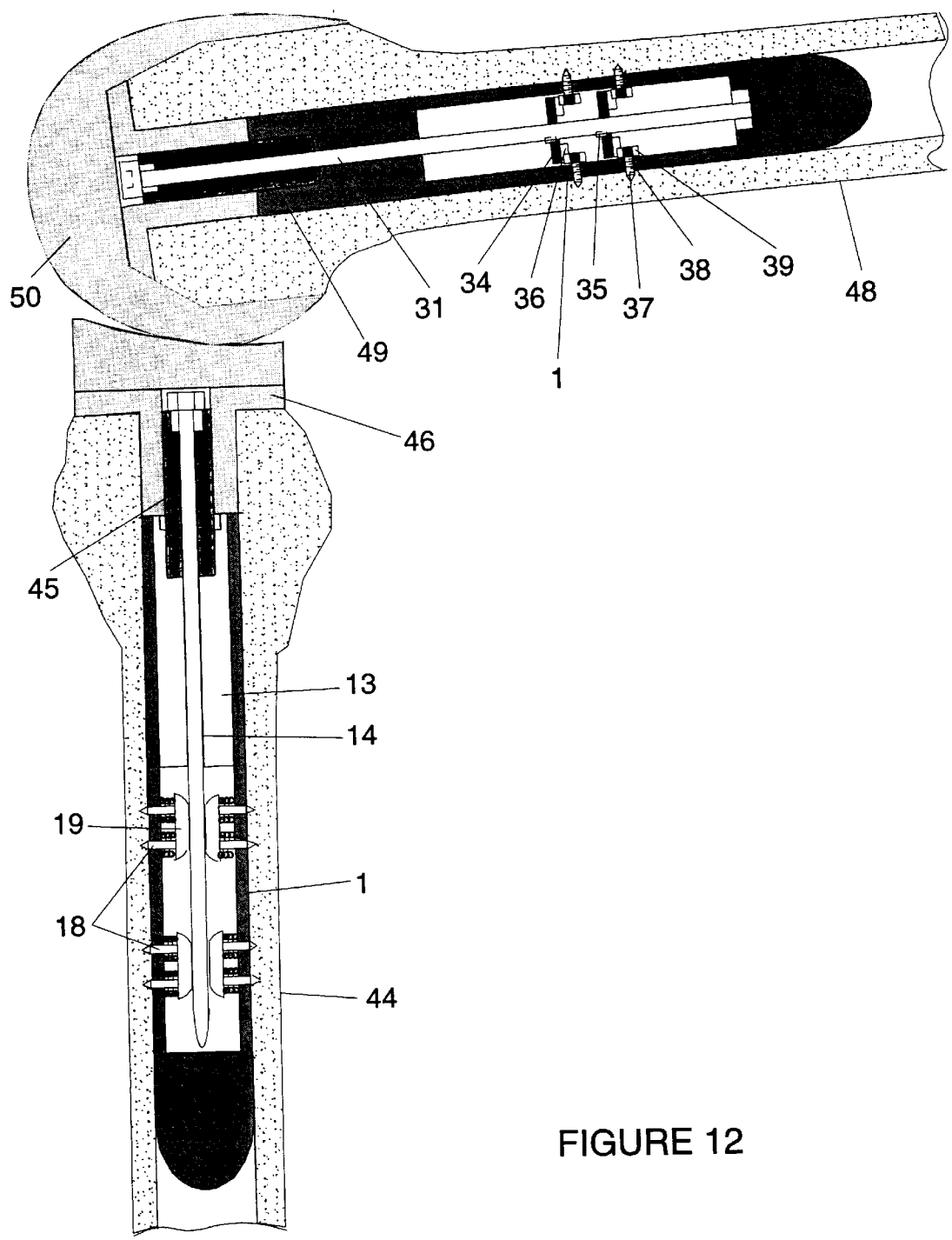
FIG. 12 is a sectional view of a knee revision showing the embodiment of the present invention as shown in FIGS. 3 and 4 in the femoral modular component, and the embodiment of the present invention as shown in FIGS. 1 and 2 in the tibial tray component.

Reference is made to FIG. 12, which shows the fixation devices 1 of the invention in use in a knee revision. By way of example, the tibia 44 contains a prosthesis having the fixation device as illustrated in FIGS. 1 and 2, and being attached to, by a coupling mechanism 45, or integral with, a tibial tray component 46. The femur 48 contains a prosthesis having the fixation device as illustrated in FIGS. 3 and 4 which is attached to, by a coupling mechanism 49, or integral with, a femoral component 50.

In the embodiment of FIGS. 5 to 7, the invention has the advantage that any impacts required to fit the prosthesis are reduced considerably. In this case it is necessary to lightly impact the plunger 22 into position. In the embodiment of FIGS. 8 and 9, the action is even simpler and smoother. There is no necessity to impact the actuating rod 31. Instead, a simple, continuous torque is applied to the rod 31, which serves to drive the screws 37 into the bone. This is expected to be much less traumatic on the bone and cause considerably reduced damage to bone tissue.

With both variants in the invention, the pins or screws serve to secure the prosthesis firmly in position. This is expected to eliminate large micromotion, i.e. movements of greater than 100 microns, and migration. Thus the prosthesis is stabilized until bone integration occurs, as a result of growth of proper bone tissue. For this purpose, the prosthesis can be provided with a porous coating to promote bone integration. If excessive micromotion is present, it has been found that fibrous tissue tends to form.

A further advantage of both techniques is that the pins 22 or screws 37 are fully retractable. For the first embodiment, the common pin head 19 can be provided with surfaces to facilitate extraction of the pins. Thus, the prosthesis could be designed so that the plunger 22 and guide insert 13 could be removed. Then, a tool can be inserted having parts that would slide between the pin heads 19 and the outer wall of the main prosthesis body 4, so as to drive the pin heads 19 back towards the axis, by a wedge action. For the second embodiment, extraction is more straight forward. It is simply a matter of rotating the actuating rod in the reverse direction, so that the gear mechanism withdraws the screws. Then, the prosthesis can be removed, if this is required to deal with problems of infection and the like.

Figure 13:
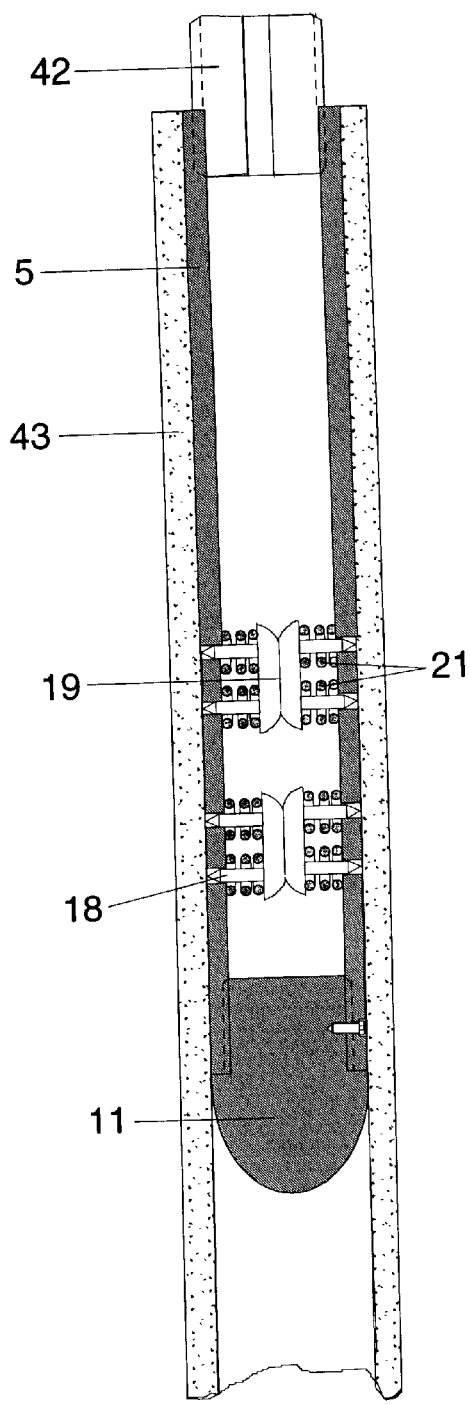
FIG. 13 is a side, sectional view through a third embodiment of a prosthesis according to the present invention, adapted for laboratory testing, shown mounted within a sheep femur.
Figure 14:
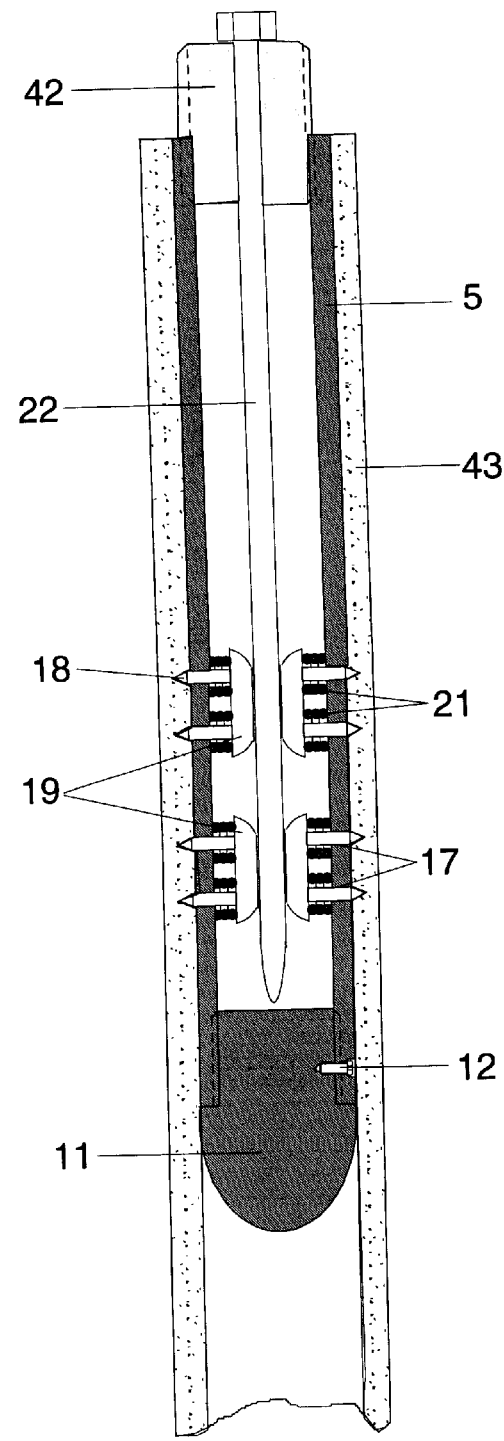
FIG. 14 is a side sectional view similar to FIG. 13, after driving of the pins into the bone.

Reference will now be made to FIGS. 13 to 16 which illustrate a test carried out in accordance with the present invention. This was based on using a prosthesis similar to that shown in FIGS. 5 and 6 using the fixation mechanism shown in FIGS. 1 and 2. The prosthesis used in the test is shown in FIGS. 13 and 14. The device includes 2 pairs of staples or heads 19 and corresponding pins 18, for a total of eight pins 18. For test purposes, it comprises just the lower, cylindrical part 5 of the first embodiment. The proximal or upper end of this part was threaded, to permit attachment to a mechanical testing machine, for performing a pull out test. A threaded connector 42 was provided for connection to a tensile testing machine, in known manner. The implant stem was then fitted into a hole or cavity drilled the same diameter as the prosthesis stem (no interference), and reamed along the center line of the shaft of a sheep femur 43. This was done in such a manner that the implant or prosthesis could be fitted into the femoral shaft by applying light impacts.

Figure 15:
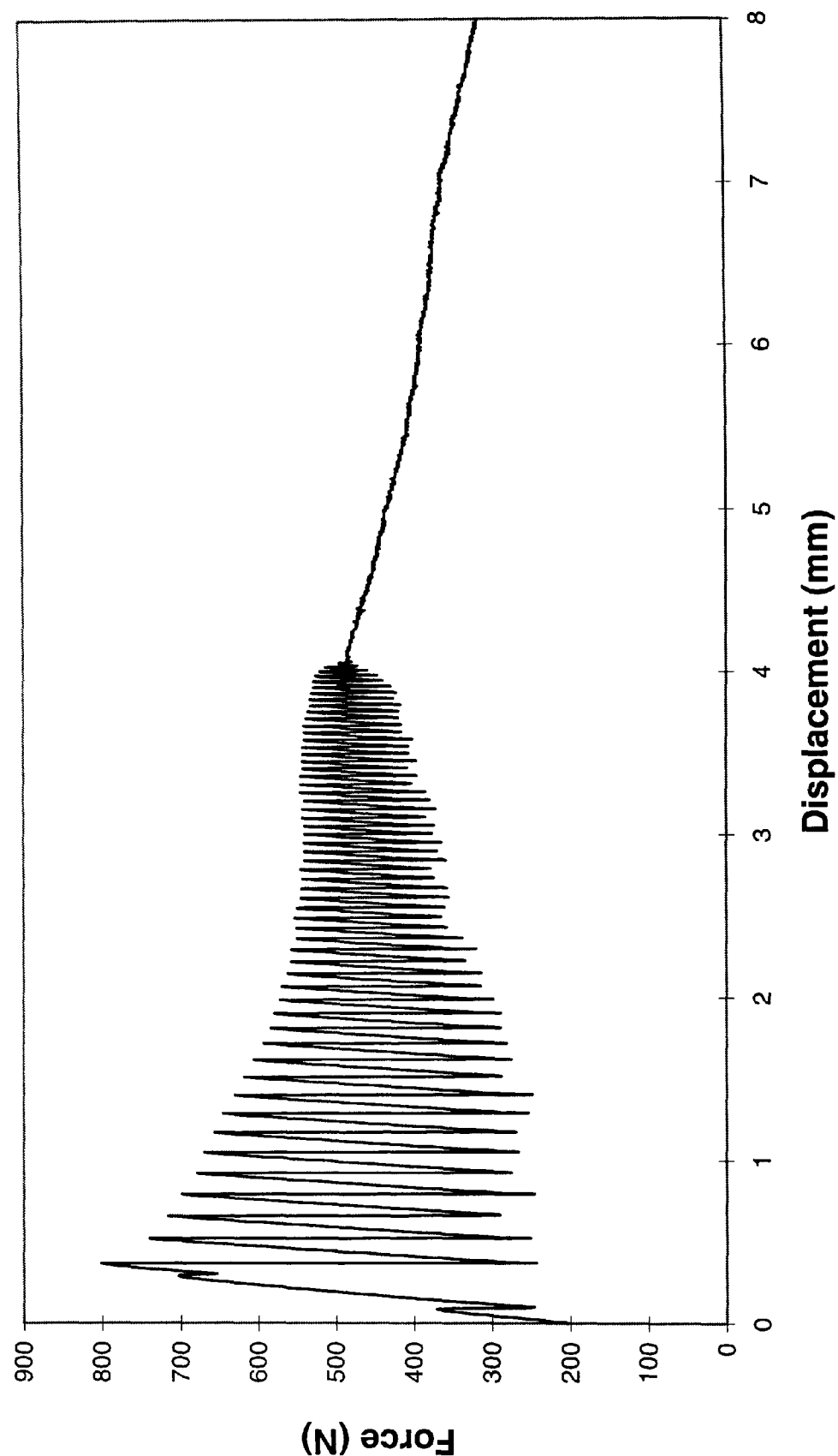
FIG. 15 is a graph showing a force-displacement diagram of a pull out test for the mounting arrangement of FIG. 13 with a tight fit using light impacts.

Initially, the prosthesis was driven into the shaft using light impacts, but the pins 18 were not actuated and the plunger 22 was omitted (FIG. 13). Then, a first pull out test was carried out. This is shown in FIG. 15. As shown in FIG. 15, no great force is required to pull out the prosthesis. It also shows that once initial slippage started to occur, subsequent displacement occurred in a jerky or irregular manner. The force would build up, and then be released, this process being repeated many times, before final removal. This test shows that a light fitting without the use of pins provides very poor mounting and pull out resistance.

The prosthesis was then refitted into the hole or cavity in the same sheep femur by applying very light impacts to its end. The plunger 22 was provided and the fixing mechanism was then actuated to drive the pins 18 into the bone (FIG. 14).

The pins were driven into the bone by applying five light impacts on the plunger shaft with a one minute recovery after impact. After penetration of the pins, an X-ray of the implant—bone assembly was taken. This showed that the pins penetrate into the bone very well without causing any local cracking of the bone.

Figure 16:
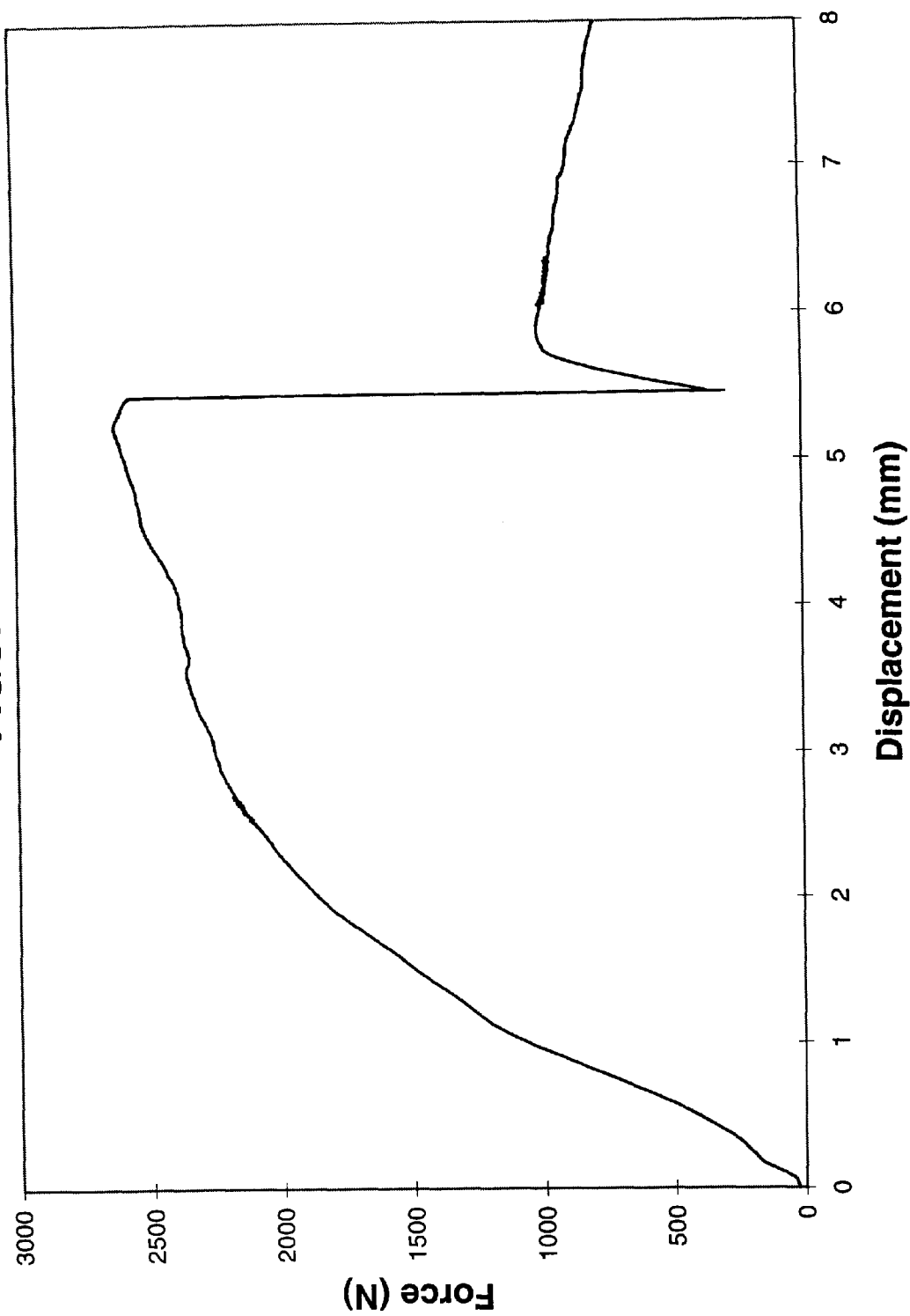
FIG. 16 is a graph showing a force-displacement diagram of a pull out test for the mounting arrangement of FIG. 14 after refitting of the prosthesis using fixation reinforcement (with the pins inserted into the bone).

The pull out test was then again repeated and the result is shown in FIG. 16. It can first be noted that until failure occurred, the curve is relatively smooth, indicating secure fixing of the prosthesis. More significantly, the maximum load recorded is over three times that for the first test, and the maximum load peaks at a force in excess of 2,700 newtons.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A prosthetic device implantable into skeletal bone, the device comprising:
    (a) a body, which includes a hollow stem part defining an internal passageway and including a plurality of openings extending between the internal passageway and the exterior of the body, the body being implantable into a cavity in skeletal bone;
    (b) a plurality of pins, with each pin being mounted in a respective opening for sliding movement between a retracted position in which the pin does not extend outside the body and an extended position in which the pin extends through the respective opening into surrounding bone to secure the device;
    (c) for each pair of pins, a common pin head secured to and joining no more than two pins; and
    (d) a plunger slidably mounted within the body and having a first end extending out of the body for actuation thereof and a second end adapted to engage the pin heads to displace the pin heads out through the openings.

2. A device as claimed in claim 1, wherein the pin heads and the second end of the plunger include cooperating cam surfaces.

3. A device as claimed in claim 2, wherein the pins are arranged so that the pin heads are mounted in pairs abutting each other in a rest position and the pins include springs biasing the pin heads towards one another.

4. A device as claimed in claim 3, which includes means, engageable with the body for securing the plunger in a position in which the pins extend out through the body.

5. A device as claimed in claim 1, which comprises a prosthesis for a hip, which includes a prosthesis head and a top surface offset to one side of the head, wherein the internal passageway of the body is straight and opens onto the top surface, and is generally perpendicular thereto.

6. A prosthetic device as claimed in claim 1 wherein the device comprises an intramedullary rod, nail, or stem.

7. A prosthetic device as claimed in claim 1 wherein the device comprises a revision of a joint.

8. A prosthetic device as claimed in claim 1 wherein the device comprises a prosthesis for a knee revision.

9. A method of mounting a prosthetic device as claimed in claim 1 the method comprising mounting the prosthesis in a cavity in bone and driving the plunger means into the body using a plurality of impacts, and providing at least one minute of recovery time after each impact.

10. A prosthetic device implantable into skeletal bone, the device comprising:
    (a) a main body defining an internal passageway and being implantable into skeletal bone, and having a plurality of openings extending between the internal passageway and the exterior of the main body, each opening being threaded;
    (b) a plurality of screws, each screw being threadably mounted in a respective opening, being adapted to cut into bone and including a gear at an end thereof;
    (c) an actuating rod, rotatably mounted in the body; and
    (d) drive gears mounted on the actuating rod and meshing with respective gears on the screws, whereby rotation of the actuating rod rotates the screws.

11. A device as claimed in claim 10, wherein the screws are provided with spur gears and the drive gears comprise crown gears meshing with the spur gears.

12. A prosthetic device as claimed in claim 10, wherein the device comprises a prosthesis for a hip joint.

13. A method of mounting a prosthetic device as claimed in claim 10 wherein the method comprises mounting the prosthesis into a cavity in bone, and actuating the actuating means to cause the screws to rotate and to penetrate bone smoothly and progressively.

14. A prosthetic device as claimed in claim 10 wherein the device comprises an intramedullary rod, nail, or stem.

15. A prosthetic device as claimed in claim 10 wherein the device comprises a revision of a joint.

16. A prosthetic device as claimed in claim 10 wherein the device comprises a prosthesis for a knee revision.

17. A prosthetic device implantable into skeletal bone, the device comprising:
  (a) a main body implantable into skeletal bone, and having a straight axis, an internal passageway around the axis, a plurality of openings extending between the internal passageway and the exterior of the main body, a head offset from the axis of the main body and a top surface offset from the head and generally perpendicular to the axis of the main body onto which top surface the internal passageway opens;
  (b) a plurality of pins provided within the internal passageway and displaceable between a retracted position within the internal passageway and an extended position extending out through the openings and penetrating bone;
  (c) drive means for displacing the pins between the retracted and extended positions; and
  (d) means, extending from the drive means to a position adjacent the top surface, for actuation of the drive means.

18. A device as claimed in claim 17, wherein each pair of pins has a common pin head, and the pin heads are arranged facing one another, and wherein the means for actuation of the drive means comprises a plunger slidably mounted in the main body and displaceable between an upper position in which the pins are retracted and a lower position in which the plunger displaces the pins and the pin heads radially outwards, so that the pins extend out from the main body.

19. A device as claimed in claim 17, wherein the pins comprise screws, wherein the openings in the main body are threaded and each screw is mounted in a respective threaded opening, and wherein the drive means comprises gears and the means for actuation of the drive means comprises an actuation rod rotatably mounted in the main body and having a first end accessible from outside the main body for rotation thereof and a second end connected to and driving the gears.

20. A device as claimed in claim 19, wherein the gears comprise crown gears and spur gears.

21. A device as claimed in claim 20, wherein the flank length of the teeth of the crown gears is sufficiently long relative to the length of the teeth of the spur gears so that the teeth of the spur gears mesh continuously with the teeth of the crown gears as the screws are rotated from a retracted position to an extended position.

22. A prosthetic device as claimed in claim 17 wherein the device comprises an intramedullary rod, nail, or stem.

23. A prosthetic device as claimed in claim 17 wherein the device comprises a revision of a joint.

24. A prosthetic device as claimed in claim 17 wherein the device comprises a prosthesis for a knee revision.

* * * * *